(12) United States Patent
Heimdal (10) Patent No.: US 12,167,937 B2
(45) Date of Patent: Dec. 17, 2024

(54) METHODS AND SYSTEMS FOR LIVE IMAGE ACQUISITION

(71) Applicant: GE Precision Healthcare LLC, Wauwatosa, WI (US)

(72) Inventor: Andreas Heimdal, Oslo (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 390 days.

(21) Appl. No.: 17/457,618

(22) Filed: Dec. 3, 2021

(65) Prior Publication Data
US 2023/0172585 A1   Jun. 8, 2023

(51) Int. Cl.
| | |
|---|---|
| A61B 8/08 | (2006.01) |
| A61B 8/00 | (2006.01) |
| G06T 5/50 | (2006.01) |
| G06T 5/77 | (2024.01) |
| G06T 7/20 | (2017.01) |

(52) U.S. Cl.
CPC ............ *A61B 8/5276* (2013.01); *A61B 8/461* (2013.01); *A61B 8/54* (2013.01); *G06T 5/50* (2013.01); *G06T 5/77* (2024.01); *G06T 7/20* (2013.01); *G06T 2207/10132* (2013.01); *G06T 2207/30004* (2013.01)

(58) Field of Classification Search
CPC ......... A61B 8/5276; A61B 8/461; A61B 8/54; G06T 5/77; G06T 5/50; G06T 7/20; G06T 2207/10132; G06T 2207/30004
See application file for complete search history.

(56) References Cited

U.S. PATENT DOCUMENTS

| | | | |
|---|---|---|---|
| 6,201,900 B1 | 3/2001 | Hossack et al. | |
| 8,469,890 B2 | 6/2013 | Langeland et al. | |
| 10,390,796 B2 | 8/2019 | Fan et al. | |
| 2006/0293598 A1 | 12/2006 | Fraser | |
| 2010/0185085 A1 | 7/2010 | Hamilton | |
| 2010/0185093 A1 | 7/2010 | Hamilton | |
| 2015/0150535 A1* | 6/2015 | Fan | A61B 8/485 600/438 |
| 2015/0201910 A1* | 7/2015 | Zhao | A61B 8/5276 600/440 |
| 2018/0042466 A1* | 2/2018 | Kang | A61B 1/00193 |
| 2018/0146955 A1* | 5/2018 | Kruecker | A61B 8/5246 |

FOREIGN PATENT DOCUMENTS

| | | |
|---|---|---|
| JP | 2006519048 A | 8/2006 |
| KR | 20150065158 A | 6/2015 |

* cited by examiner

*Primary Examiner* — John J Lee
(74) *Attorney, Agent, or Firm* — McCoy Russell LLP (57) ABSTRACT

Various methods and systems are provided for display of live images. In one example, a method for motion compensation in the live images includes acquiring a first set of imaging data from a visible sector of an imaging system, the visible sector including a region of interest displayed to a user, and acquiring a second set of imaging data at an area offset from the visible sector, during the acquiring of the first set of imaging data. The second set of imaging data is used to compensate for gross motion of the region of interest resulting in displacement of at least a portion of the region of interest outside of the visible sector.

19 Claims, 6 Drawing Sheets

METHODS AND SYSTEMS FOR LIVE IMAGE ACQUISITION

FIELD

Embodiments of the subject matter disclosed herein relate to ultrasound imaging.

BACKGROUND

Ultrasound imaging utilizes high-frequency sound waves to produce images of organs, tissues, or blood flow. The sound waves are generated by an ultrasound probe or transducer and transmitted in pulses. Reflection of the sound waves by boundaries between organs, tissues, bones, etc., are detected by the probe and relayed to a control unit where the reflected waves are converted to a two-dimensional or three-dimensional image.

Information provided by images produced by an ultrasound imaging system may be affected by conditions during image acquisition. More specifically, analysis of the images for diagnosing a patient's condition may be affected by image quality and a completeness of an imaging data set. The conditions may include movement, such as gross motion, occurring during image collection. For example, the ultrasound probe may move during acquisition due to movement of an operator holding the probe. Additionally or alternatively, a patient undergoing imaging may move and/or an anatomical region of interest the patient may be in motion within a visible sector of the ultrasound probe that is displayed to a user.

BRIEF DESCRIPTION

In one embodiment, a method for motion compensation in live images includes acquiring a first set of imaging data from a visible sector of an imaging system, the visible sector including a region of interest displayed to a user, acquiring a second set of imaging data, at an area offset from the visible sector, during the acquiring of the first set of imaging data, and using the second set of imaging data to compensate for gross motion of the region of interest resulting in displacement of at least a portion of the region of interest outside of the visible sector. In this way, the images may be displayed in a more stable and reliable manner without loss of data due to the gross motion.

In one example, acquiring the second set of imaging data from the area offset from the visible sector includes determining a positioning of a buffer region relative to the visible sector. An acquisition beam angle may be adjusted according to the buffer region to collect additional data from areas outside of the visible sector where the gross motion is likely to occur. The additional data may be collected regardless of whether the additional data is used or included in image frames displayed to the user. The visible sector that is displayed to the user, as well as an image of the region of interest, may remain unchanged however, thus maintaining an amount of detail of the region of interest that may be readily viewed by the user.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
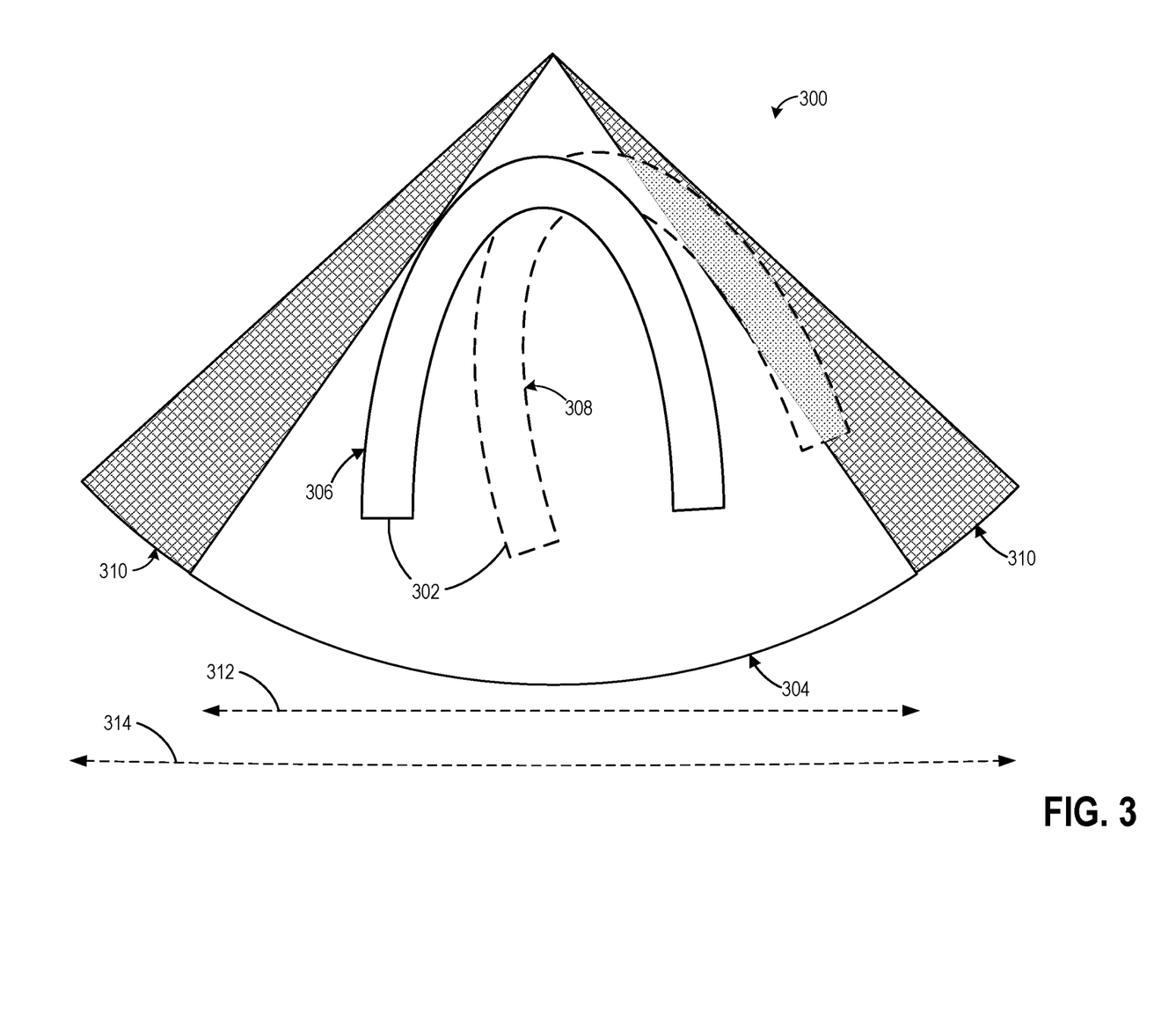
FIG. 3 shows a first example of an imaging sector of the imaging system of FIG. 1 with additional data collected from a region outside of the imaging sector.
Figure 4:
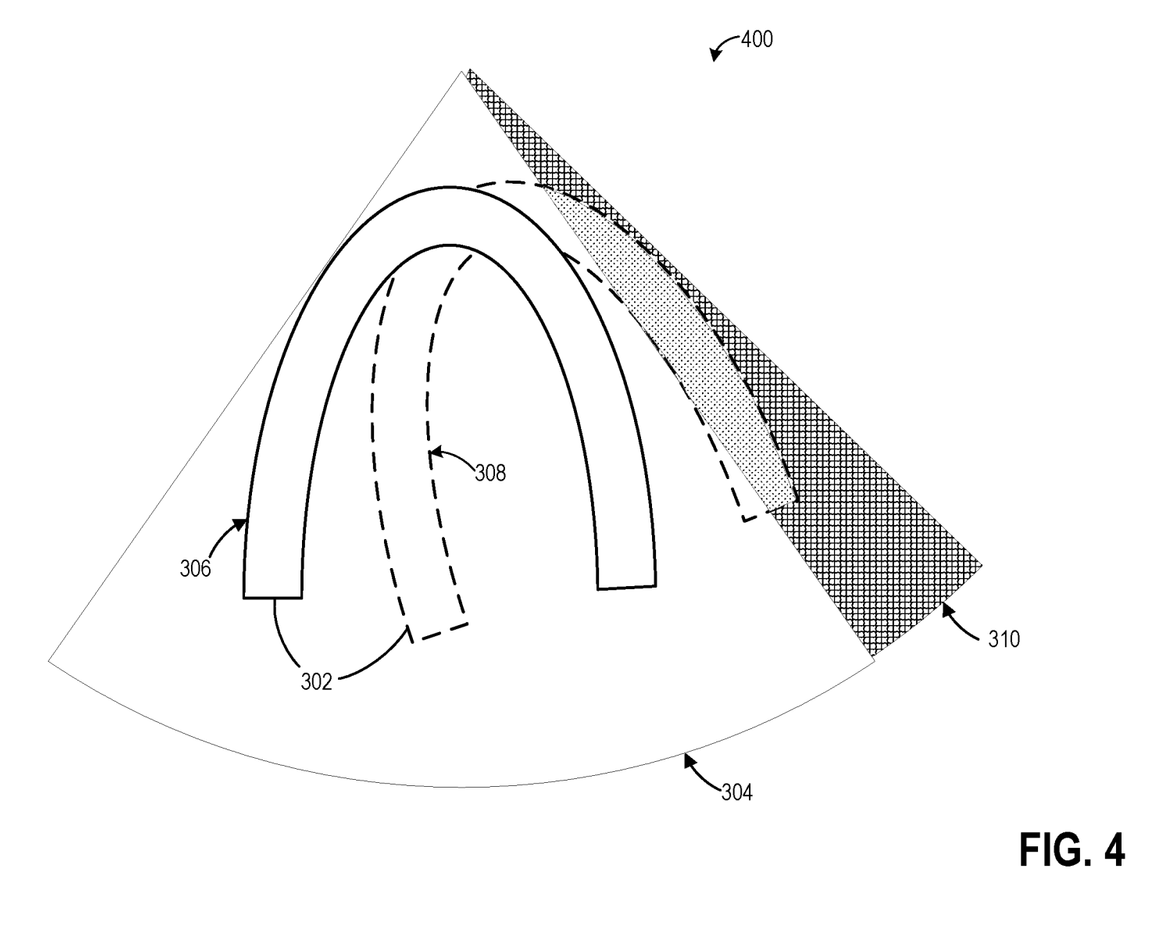
FIG. 4 shows a second example of an imaging sector of the imaging system of FIG. 1 with additional data collected from a region outside of the imaging sector.
Figure 5:
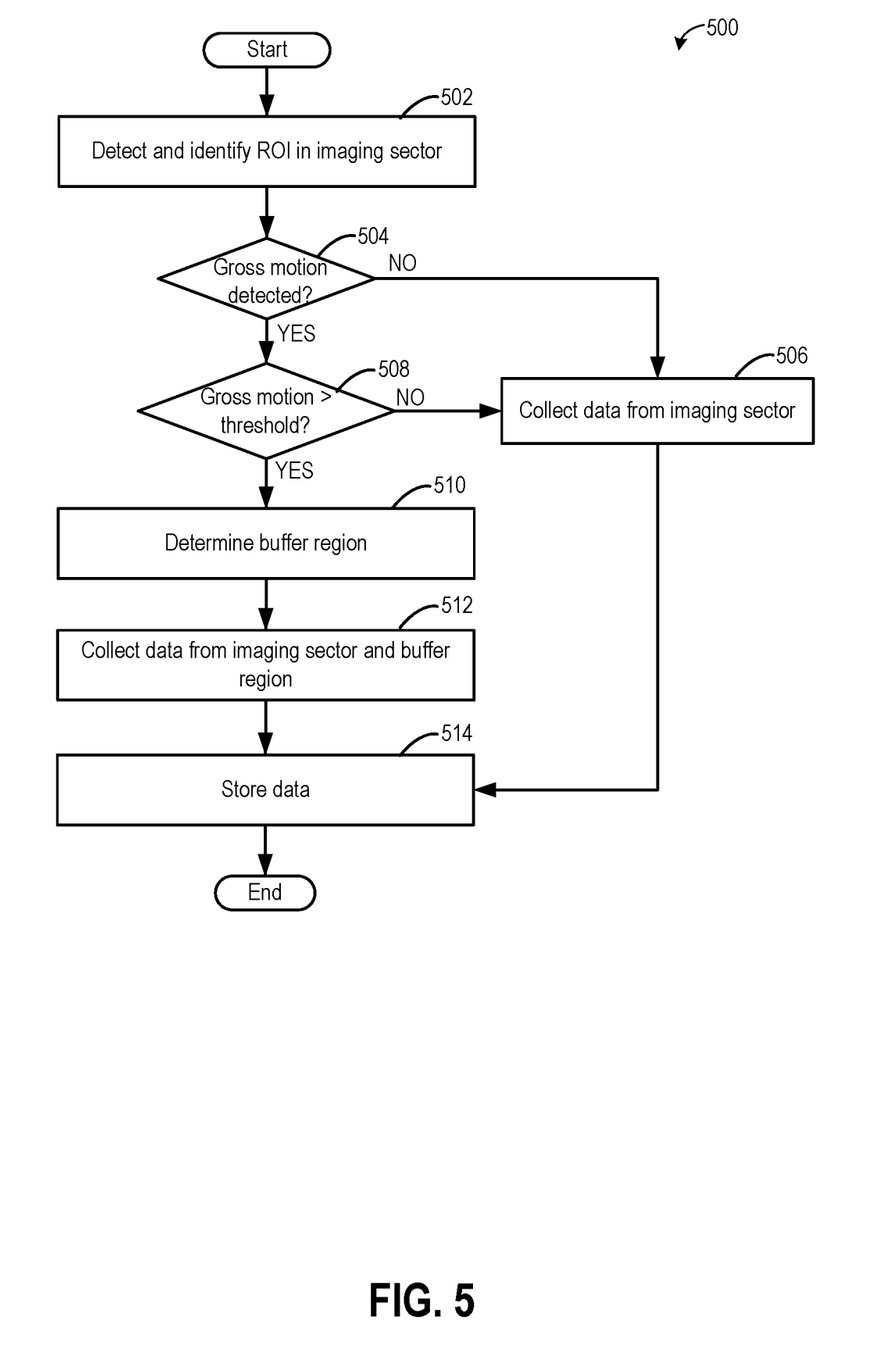
FIG. 5 shows an example of a method for collecting imaging data in addition to data acquired from a visible sector of an imaging system when gross motion of an imaging region of interest is detected.

The following description relates to a method for image acquisition from an imaging system. In one example, the imaging system may be an ultrasound imaging system and images may be acquired via an ultrasound probe. The method may provide a strategy for motion compensation by tracking gross motion of an imaging object, where gross motion is movement that affects a relative position of the imaging object. As such, the gross motion is an overall motion of the object, excluding motion differences within the imaging object, such as contractions within a ventricle muscle of a heart. The imaging object may be a region of interest (ROI) of an area that is displayed as an image, where the area that is displayed as the image is also referred to herein as a visible sector or an imaging sector. The ROI may be, for example, an anatomical feature such as an organ, tissue, arteries and veins, etc. In some instances, the gross motion may cause at least a portion of the ROI to be displaced outside of the visible/imaging sector of the ultrasound probe. In order to mitigate loss of data leading to incomplete display or analysis of the acquired images, movement of the ROI may be tracked and additional data may be collected from outside of the visible sector to compensate for the movement of the ROI. The additional data may be obtained from a buffer region that is offset from the visible sector, as shown in FIGS. 3 and 4. The buffer region may be applied according to a tailored method for motion tracking during image acquisition, as depicted in FIG. 5. Image data acquired via the method of FIG. 5 may be processed to provide a stable and complete display of the images according to a method shown in FIG. 6.

The tailored motion tracking technique described herein may be applied to various types of imaging modes and as well as imaging device types and geometries used to obtain the images. Furthermore, the technique may be for both two-dimensional (2D) and three-dimensional (3D) imaging. In some examples, the technique may be selectively applied according to observed and/or anticipated motion of the object to be imaged, e.g., the technique may include real-time application. As such, details of the images may not be lost due to motion of the object or at an imaging device. While examples of an ultrasound system and motion tracking of images obtained by the ultrasound system are presented below, the object tracking and motion compensation may be applied to other types of images, such as x-ray fluoroscopy images.

Figure 1:
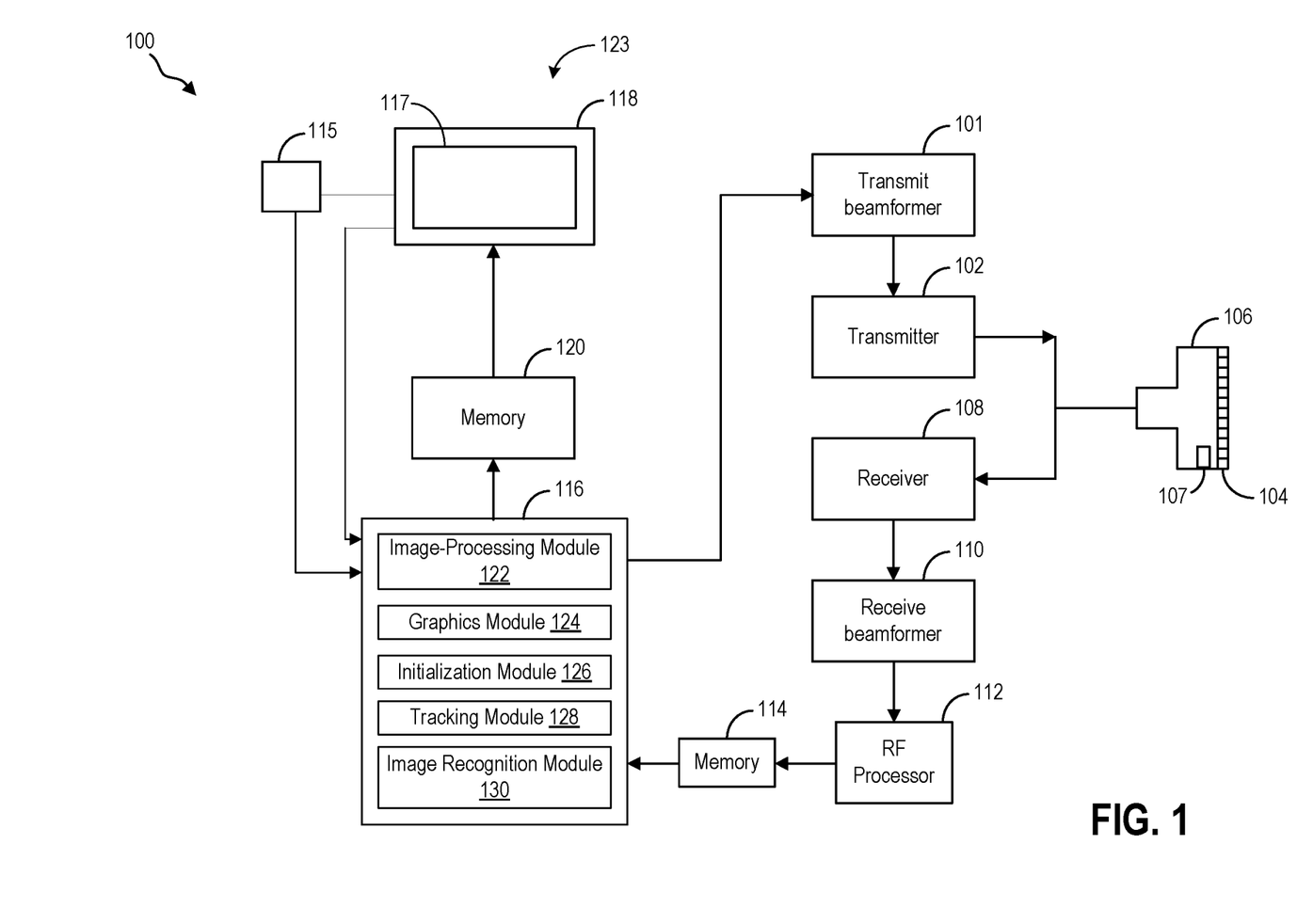
FIG. 1 shows an example of an imaging system.

Before further discussion of the approach for compensating for gross motion in ultrasound imaging, an example platform for implementation of the approach is shown in FIG. 1. Therein, a block diagram of a system 100 is depicted, according to one embodiment. In the illustrated embodiment, the system 100 is an imaging system and, more specifically, an ultrasound imaging system. As shown, the system 100 includes multiple components. The components may be coupled to one another to form a single structure. In one example, the system 100 is a unitary system that is capable of being moved (e.g., portably) from room to room. For example, the system 100 may include one or more components configured to couple the system 100 to a wheeled cart. However, in other examples, at least portions of the system 100 may be configured to remain stationary and/or fixed in place.

In the illustrated embodiment, the system 100 includes a transmit beamformer 101 and transmitter 102 that drives an array of elements 104 (e.g., piezoelectric crystals) within a diagnostic ultrasound probe 106 (or transducer) to emit pulsed ultrasonic signals into a body or volume (not shown) of a subject. The elements 104 and the probe 106 may have a variety of geometries. For example, the probe 106 may be a sector probe, a linear probe, a convex probe, a curvilinear probe, a phase array probe, etc. The ultrasonic signals are back-scattered from structures in the body, for example, blood vessels and surrounding tissue, to produce echoes that return to the elements 104. The echoes are received by a receiver 108. The received echoes are provided to a receive beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system 100 also includes a system controller 116 that includes a plurality of modules, which may be part of a single processing unit (e.g., processor) or distributed across multiple processing units. The system controller 116 is configured to control operation of the system 100. For example, the system controller 116 may include an image-processing module 122 that receives image data (e.g., ultrasound signals in the form of RF signal data or IQ data pairs) and processes image data. For example, the image-processing module 122 may process the ultrasound signals to generate slices or frames of ultrasound information (e.g., ultrasound images) for displaying to the operator. The image-processing module 122 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography, speckle tracking, and chamber quantification. The generated ultrasound images may be 2D or 3D. When multiple 2D images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the controller 116) and displayed to the operator or user on the display device 118.

The system controller 116 is operably connected to a user interface 123 that enables an operator to control at least some of the operations of the system 100. The user interface 123 may include hardware, firmware, software, or a combination thereof that enables an individual (e.g., an operator) to directly or indirectly control operation of the system 100 and the various components thereof. As shown, the user interface 123 includes a display device 118 having a display area 117. In the examples described herein, the display device 118 is a touchscreen display that enables the operator to adjust operating parameters of the system 100 by directly interacting with (e.g., touching) the display device 118. For example, the display device 118 may be configured such that when the user moves a finger/glove/stylus across the face of the display device 118, a cursor atop the ultrasound image on the display area 117 moves in a corresponding manner. The display device 118 may detect a presence of a touch from the operator on the display area 117 and may also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the controller 116 to the operator by displaying the information to the operator. The display device 118 and/or the user interface 123 may also communicate audibly. The display device 118 is configured to present information to the operator during the imaging session. The information presented may include ultrasound images, graphical elements, user-selectable elements, and other information (e.g., administrative information, personal information of the patient, and the like). In some embodiments, the user interface 123 may be additionally configured to interface with (e.g., electronically couple to) one or more user interface input devices 115, such as a physical keyboard, mouse, and/or touchpad.

In addition to the image-processing module 122, the system controller 116 may also include a graphics module 124, an initialization module 126, a tracking module 128, and an image-recognition module 130. The image-processing module 122, the graphics module 124, the initialization module 126, the tracking module 128, and the image-recognition module 130 may coordinate with one another to present information to the operator during and/or after the imaging session. For example, the image-processing module 122 may be configured to display an acquired image on the display device 118, and the graphics module 124 may be configured to display designated graphics along with the ultrasound image, such as graphical outlines, which represent lumens or vessel walls in the acquired image. The image-processing and/or graphics modules 122, 124 within the system controller 116, may also be configured to generate a 3D rendering or image (not shown) of the entire vascular structure.

The image-processing module 122 may further include various sub-modules for image processing. For example, a 2D video processor sub-module may be used to combine one or more frames generated from different types of ultrasound information. Successive frames of images may be stored as a cine loop, described further below with reference to FIG. 2, in the memory 114. The cine loop represents a first in, first out circular image buffer to capture image data that is displayed in real-time to the user. The user may freeze the cine loop by entering a freeze command at the user interface 123.

The image-processing module 122 may also include a 3D processor sub-module which may be controlled by the user interface 123 and may access the memory 114 to obtain 3D ultrasound image data. Three-dimensional images may thereby be generated through volume rendering or surface rendering algorithms, for example, as well as techniques such as ray-casting, maximum intensity pixel projection, etc.

The tracking module 128 may also be controlled by the user interface 123 and retrieves ultrasound information from the memory 114 to generate motion tracking information for display. As such, the tracking module 128 may receive processed data from the image-recognition module 130 which may include algorithms for detecting and identifying an object, such as a ROI, within an imaging sector (or visible sector) of the probe 106. The imaging sector may be a region of the FOV of the probe 106 defined by a sector beam of the probe 106 that is displayed to the user at the user interface 123 and frames presented in the cine loop may be acquired from the imaging sector. The image-recognition module 130 may include capabilities for analyzing imaging sectors, identifying ROIs within the imaging sectors, such as a heart, liver, lungs, blood vessels, and/or other organs, tissue, and/or structures. Data processed by the image-recognition module 130 that is sent to the motion tracking module 128 may include indicators to track a position of an identified ROI amongst a set of live images acquired during an imaging session. The motion tracking module may include motion tracking algorithms for monitoring movement in the identified ROI.

In one example, the motion tracking capability of the tracking module may be enabled by speckle tracking. In speckle tracking, speckle information in acquired images are used to track motion of the ROI. For example, naturally occurring speckle patterns in myocardium of a heart may be tracked, where the tracking may be enabled by various block-matching techniques. The block-matching techniques may include similarity measures such as sum of absolute differences or cross-correlation. Other motion tracking techniques may include contour tracking, where contours may be detected in an image and tracked over time, and optical flow, in which changes in brightness patterns are analyzed over time.

The tracking module 128 may also include algorithms for motion compensation which enables removal of gross motion from displayed images. The motion compensation algorithms may provide instructions to scale, rotate, and/or translate the images to reduce gross motion from the images.

Gross motion may be detected based on algorithms for speckle tracking or border detection, implemented at the tracking module 128. In some instances, the tracking module may receive signals from one or more motion sensors 107 embedded into the probe 106 that detect motion at the ROI. For example, the probe 106 may include an optical marker and one or more cameras filming the probe 106. A processing unit may be used to analyze images from the one or more cameras to estimate motion of the probe 106. As another example, the probe 106 may include accelerometers to provide signals which may be used to estimate probe motion. In yet another example, a magnetic position sensor may be used. Additionally, hybrid variants using both image analysis and the motion sensors are possible.

In some instances, the tracking module 128 may be configured to determine a boundary or border of the ROIs which may be tagged, for example, and/or tracked to monitor a relative position of the ROIs within the sector. In another example, segmentation algorithms may be applied to an image captured within the sector to identify and track the ROIs. For example, various segmentation techniques, such as detection of regions, threshold, edges, clusters, etc., may be used to partition the image into segments where each segment includes image pixels that share a common property.

The image-recognition module 130 may access stored images/videos (e.g., an image library) from either or both of the memory 114 and the memory 120, before analyzing them. For example, knowing the parameters under which a protocol is being carried out (ultrasound type, scan plane, tissue being imaged, etc.) the image-recognition module 130 may compare a live image on the display area 117, to one stored in memory 120, in order to analyze the image and thereby improve the accuracy of placing and utilizing analytical tools. In an alternative embodiment, instead of utilizing the image-recognition module 130 and image library, the system controller 116 may house instructions for analyzing acquired imaging data (e.g., ultrasound images/videos acquired with the probe) and automatically determining a desired placement of one or more analytical tools, such as a region of interest.

The screen of the display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity, color flow velocity, texture, graininess, contractility, deformation, and rate of deformation value. The series of pixels then make up the displayed image generated from the acquired ultrasound data.

Figure 2:
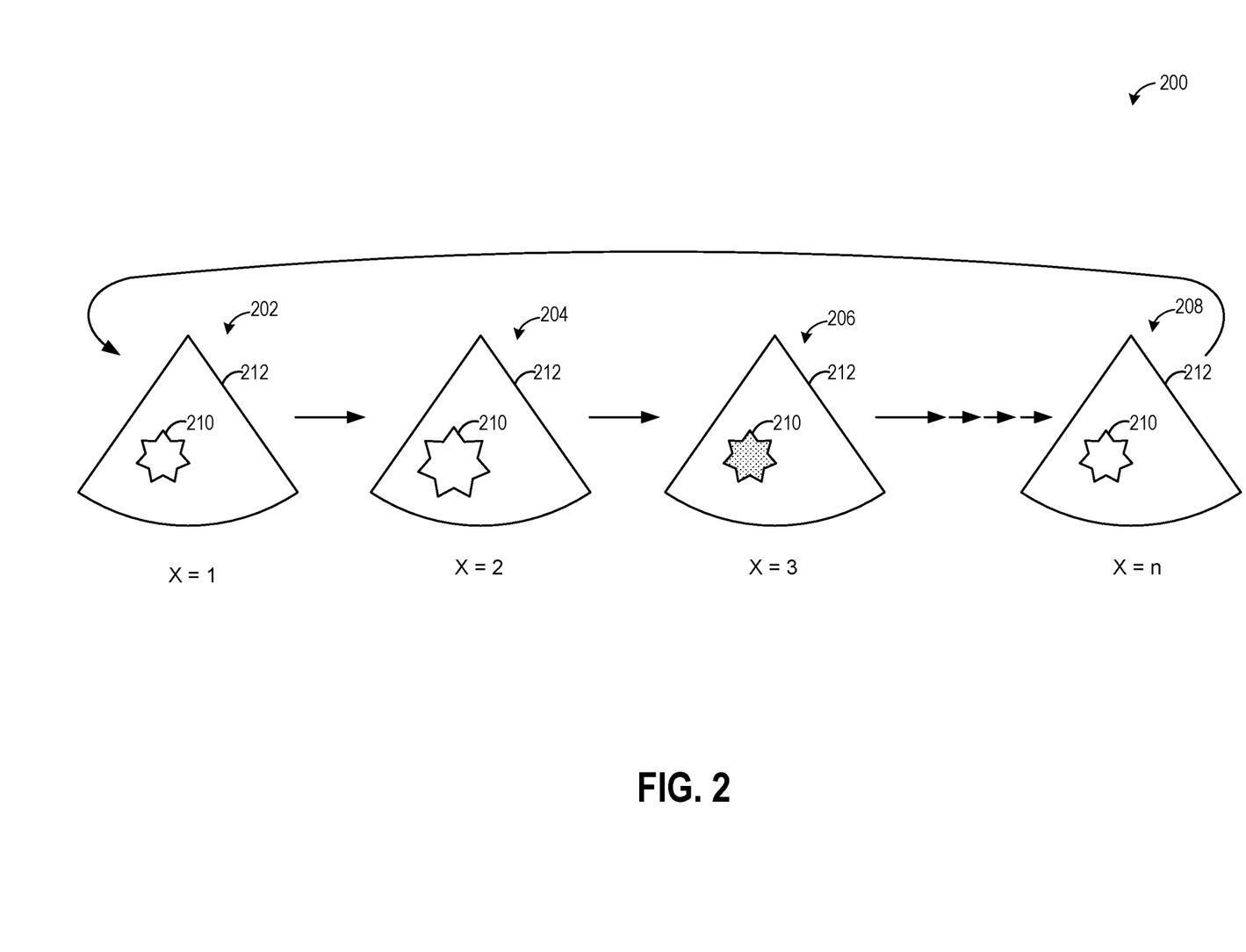
FIG. 2 shows an example of a cine loop for displaying images from the imaging system of FIG. 1.

As described above, ultrasound images may be collected successively and the successive images may be displayed to the user as an imaging loop, such as a cine loop. The cine loop presents a set number of successive image frames as a dynamic display of a region of interest (ROI), e.g., similar to a short video. For example, a cine loop 200 is represented in FIG. 2. The cine loop 200 relies on a set of image frames obtained, for example, from an ultrasound imaging system.

The set of image frames are arranged according to a chronological sequence. For example, a first image frame 202 may be a first captured image (e.g., x=1 where x is a chronological order of an image according to acquisition time) of the set of image frames. A second image frame 204 may be acquired after the first image frame 202, and a third image frame 206 may be acquired after the second image frame 204. The sequence continues until a target number, n, of images are obtained, as indicated by a final image frame 208 of the set of image frames. When requested by a user, the cine loop 200 is displayed to the user at a user interface, e.g., the user interface 123 of FIG. 1, as a continuous loop. For example, each image frame of the set of image frames is displayed sequentially according to a time frame, e.g., a duration between image acquisitions, similar to an image acquisition frequency used to capture the images. When the final image frame 208 is displayed, the cine loop returns to the first image frame 202.

An ROI 210 may be a target imaging object within an imaging sector 212 of each of the set of image frames. In one example, the ROI 210 may be an anatomical feature that is associated with gross motion. The gross motion may cause the ROI 210 to move relative to boundaries of the imaging sector 212 of the first image frame 202 in subsequently acquired image frames. However, motion compensation algorithms may be used to account for the gross motion such that the ROI 210 is maintained in a static position within the imaging sector 212 across each image frame shown in the cine loop 200. For example, the ROI 210 may experience gross motion that may temporarily alter dimensions of the ROI 210 (as illustrated in the second image frame 204) in addition to altering the position of the ROI 210 or change a shading of the ROI 210 (as illustrated in the third image frame 206) in addition to varying the position of the ROI 210. Changing/varying the position of the ROI 210 may include translation of the ROI 210 in space relative to the imaging sector 212. However, while the change in dimensions is shown in the second image frame 204 and the change in shading is shown in the third image frame 206, changes to the relative position of the ROI 210 within each of the image frames is not displayed. The relative position of the ROI 210 within the imaging sector 212, remains consistent amongst the set of image frames of the cine loop 200.

By maintaining the position of the ROI 210 static in the cine loop 200, the ROI 210 is readily observed and assessed by the user. However, the gross motion of the ROI 210 may cause the ROI 210 to shift temporarily beyond the boundaries of the imaging sector 212. In such instances, at least a portion of data specific the ROI 210 may be lost in image frames of the cine loop 200 where at least a portion of the ROI 210 moves outside of the imaging sector 212. As such, the cine loop 200 may include time points or moments where the ROI 210 appears to skip or is missing data.

Other issues may arise from gross motion during image acquisition. As described above, the gross motion may result from movement of the imaged object. In other examples, the gross motion may be due to movement of an imaging device, such as an ultrasound probe. In addition to adverse effects on image/data display, e.g., as a cine loop, such movement may also present challenges with respect to post-processing of ultrasound images when the ROI is moving within the image frames, e.g., the relative position of the ROI varies. In order to efficiently analyze and process data from the ROI over time, removal of the gross motion, e.g., by motion compensation algorithms, is desirable. Removal of the gross motion allows the ROI to be presented in a fixed position in the cine loop, as an example. In addition, for systems applying thermal therapy (e.g., high intensity focused ultrasound), to a target tissue region, gross motion of the target tissue may cause the thermal therapy to affect tissue regions where the thermal therapy is not desired.

In one example, the issues described above may be addressed by a motion tracking strategy that allows additional imaging data to be collected outside of an imaging region displayed to the user, e.g., outside of an imaging sector. The motion tracking strategy may circumvent skipping of analysis and/or display of data at time points or image frames where at least a portion of the ROI is outside of the imaging sector. A more complete set of results may be obtained and/or a more stable display of the results may be enabled.

Additionally, the motion tracking strategy may obviate a reliance on modeling of the gross motion and/or display of data for the time points or image frames where at least a portion of the ROI is outside of the imaging sector. More complete and accurate results may be available to the user as a result. As well, image acquisition using a sector size that is similar to the ROI is enabled. As a result, the image of the ROI may appear sufficiently large on a display device, such as the display device 118 of FIG. 1, to allow the user to readily assess the ROI during live imaging while additional data from outside of the imaging sector is collected to be used for gross motion compensation.

As described above, gross motion during image acquisition may cause an ROI to move outside of an imaging sector (e.g., a visible sector displayed to a user) of an imaging system or device. An example of such movement is depicted in FIG. 3. Therein, a first example of an imaging data set 300 illustrating representative time-lapsed images of a ROI 302, within an imaging sector 304 of an ultrasound imaging system, is shown. In one example, the ROI 302 may be a heart. The imaging data set 300 includes a first position 306 of the ROI 302, captured in a first frame, and a second position 308 of the ROI 302, captured in a second frame.

In the first frame, the first position 306 of the ROI 302 depicts the ROI 302 positioned entirely within boundaries of the imaging sector 304. A complete image of the ROI 302 is therefore displayed to a user. In the second position 308, however, the ROI 302 is shifted to the right within the imaging sector 304, such that a portion of the ROI 302 (indicated as a shaded region in FIG. 3) is located outside of the imaging sector 304.

Shifting of the ROI within the imaging sector may occur intermittently across a set of frames displayed in a cine loop. In frames where at least a portion of the ROI moves beyond the boundaries of the imaging sector, e.g., as shown by the second position 308 of the ROI 302 of FIG. 3, an amount of data corresponding to the portion of the ROI positioned outside of the imaging sector may be lost. This may lead to skipping of analysis and/or display of data in frames where the ROI shifts outside of the imaging sector 304. As a result, a set of results may be incomplete and display of the results may be unstable. In some examples, the lost data may be accounted for by extrapolation of available data and/or modelling of the missing regions. An accuracy of the estimated data, however, may be low.

In one example, movement of the ROI 302 beyond boundaries of the imaging sector 304 may be addressed by a tailored strategy for tracking motion of the ROI 302 during post-processing of imaging data for live display. The live display of the imaging data includes presenting the cine loop to the user. The strategy may include obtaining a larger data set than a data set displayed to the user at the imaging sector 304. For example, a data set acquired via a wider beam angle than demanded for data constrained by boundaries of the imaging sector 304 may be captured. A portion, e.g., a central portion of the wider angle data set may be presented to the user, and a buffer region 310, where the buffer region 310 is indicated by hatching in FIG. 3, may be included in the wider angle data set, thereby allowing data to be collected in addition to data corresponding to the imaging sector 304. However, the buffer region 310 may not be displayed to the user. As such, the additional data may provide hidden, available imaging results that may be used to supplement imaging data from the imaging sector 304 that is displayed. In addition, the buffer region 310 may be applied to define where the additional data is to be acquired regardless of whether the additional data is actually used to fill in data missing from within the imaging sector 304. In other words, the additional data may be obtained when gross motion is detected, in case data is lost during an imaging session due to the gross motion, and the additional data may or may not be displayed along with the imaging data from within the imaging sector 304 depending on the gross motion at the ROI 302.

The buffer region 310 may be offset from the imaging sector 304. For example, the buffer region 310 may cover an area outside of an area of the imaging sector 304. As such, the imaging sector 304 may have a first cross-sectional width 312 and the buffer region may have a second cross-sectional width 314 that is greater than the first cross-sectional width 312.

Data may be collected in addition to and concurrently with image acquisition from within the imaging sector 304. As described above, a wider beam angle may be used to obtain data from the buffer region 310 in addition to the imaging sector 304. For example, beams may be transmitted spaced further apart from one another, e.g., low beam density, which may lower lateral resolution but may allow a frame rate to be maintained. Alternatively, the beam density may remain unchanged while the frame rate is decreased, thereby maintaining a desired resolution of the images. In some examples, a balance between applying a lower beam density and a lower frame rate may be used. In some instances, as described further below, collection of additional data from the buffer region 310 may be conducted dynamically. In such examples, the dynamic collection may cause the frame rate to vary, which may not be allowable according to image acquisition parameters, and therefore the beam resolution may be adjusted accordingly rather than the frame rate.

Although adjusting the beam angle used for image acquisition may, in some instances, concomitantly decrease beam density relative to a narrower angle, the buffer region 310 may be selected to minimize loss of resolution. A size of the imaging sector 304 displayed to the user may remain uniform, in spite of the additional available data, thus the frames presented to the user in the cine loop may retain a high level of resolution (e.g., beam density). An amount of additional data obtained from the buffer region 310 may be tuned according to a type of probe or application used to acquire the images. The additional data may be processed via motion compensation algorithms of a tracking module, e.g., the tracking module 128 of FIG. 1, and included in the set of results provided to the user to supplement omitted data from within the imaging sector 304. For example, the additional data may be fed to the motion compensation algorithms for processing and the processed data may be used by the algorithms to fill in data that is missing from the imaging data acquired from inside the imaging sector 304. As such, upon detection of gross motion at the ROI 302, e.g., by motion sensors such as the motion sensors 107 of FIG. 1 or analysis of live imaging data such as speckle tracking, data may be acquired from an expanded sector, e.g., the imaging sector 304 plus the buffer region 310, without altering a live display of the imaging sector 304. Upon post-processing of the data, the additional data from the buffer region 310 may be presented with the display of the imaging sector 304.

An amount of additional data obtained from the buffer region 310, e.g., a size of the buffer region, may be determined based on a set estimation of gross motion at the ROI 302. For example, analysis of previous analyses of ROIs of a same type may be used to infer an average amount of expected movement of the ROI type. The buffer region 310 may then be set to accommodate the set estimation of gross motion and applied during an entire imaging session. As an example, when the gross motion is estimated in real time, frame by frame, a size of the buffer region 310 (e.g., an additional sector size) may be increased from a next acquired frame to maintain the ROI 302 completely within the buffer region 310. The size of the buffer region 310 may be decreased from a subsequent frame if the gross motion is estimated to be within a smaller sector.

In another example, the gross motion may be estimated over a longer period of time, such as a full cardiac cycle, or longer, and a maximum estimated motion may be used to set a new buffer region size. Furthermore, in yet another example, a study of previously recorded images may be used to set a fixed buffer region size for a given probe/application to cover anticipated motion outside of the imaging sector 304. A combination of the methods described above may also be used, e.g., applying a fixed buffer region size initially, and adjusting the size during image acquisition.

In some examples, the collection of the additional image data may be conducted in a dynamic manner. In other words, a positioning of the buffer region 310 of FIG. 3 relative to the imaging sector 304 may be adjusted depending on how the ROI is estimated to move within a specific imaging session instead of the set estimation. For example, gross motion may occur in an unexpected manner at the ROI due to movement of the imaging device, e.g., at an ultrasound probe, or due to movement of a patient. In such instances, the gross motion may deviate from the set estimation of gross motion. In one example, when gross motion is detected during image acquisition, localization of the gross motion may be estimated, e.g., based on speckle tracking and/or signals from motion sensors, at the tracking module. The buffer region 310 may be adjusted to focus the additional data collection to be obtained regions where the gross motion is estimated to occur, according to an extent of the gross motion.

For example, a second example of an imaging data set 400 is illustrated in FIG. 4. The imaging data set 400 includes elements shown in FIG. 3, such as the imaging sector 304 and the ROI 302 in the first position 306 and the second position 308, where the second position 308 results in a portion of the ROI 302 being positioned outside of the imaging sector 304. Relative to the first example of the imaging data set 300 of FIG. 3, the buffer region 310 is biased to one region beyond the boundaries of the imaging sector 304 provide a complete image of the ROI 302 when the ROI 302 is in the second position 308.

Additional data, e.g., in addition to data collected from within the imaging sector 304, may be obtained from the localized area beyond the imaging sector 304 in order to acquire a complete imaging data set from the ROI 302. Various techniques for detecting motion outside of the imaging sector 304 may be implemented. For example, gross motion of the ROI 302 may be tracked using speckle tracking or border tracking, where portions of the ROI 302 may be followed outside of the imaging sector 304. As another example, a priori knowledge of a shape of the ROI 302 may be used in combination with border tracking to estimate a position of the ROI 302. Instances during which the a priori known shape of the ROI 302 is determined to not be fully detected inside the imaging sector 304 may be observed, as well as which portion of the ROI 302 is missing to indicate that the ROI 302 is partially outside of the imaging sector 304.

Adjustment of the buffer region 310 may be executed dynamically, e.g., in response to estimates of the gross motion of the ROI 302. As such an area covered by the buffer region 310 may not remain uniform between imaging sessions of a same type of ROI. An amount of additional data may be customized according to gross motion conditions occurring during a specific imaging session.

In another example, the tailored motion tracking strategy may be applied in real-time. For example, motion tracking algorithms or a motion sensor at an ultrasound probe, as described above, may detect motion as images are being acquired. As such, an image acquisition process may be adjusted in response to detection of the motion. In one example, acquisition of additional data outside of the imaging sector may be collected only when motion is detected. Thus application of the buffer region to collect additional imaging data may be intermittent and selective. Adjustments to an applied image acquisition process, such as modifications to frame rate and image quality/resolution, may be demanded to adapt the motion tracking strategy to real-time application.

Figure 6:
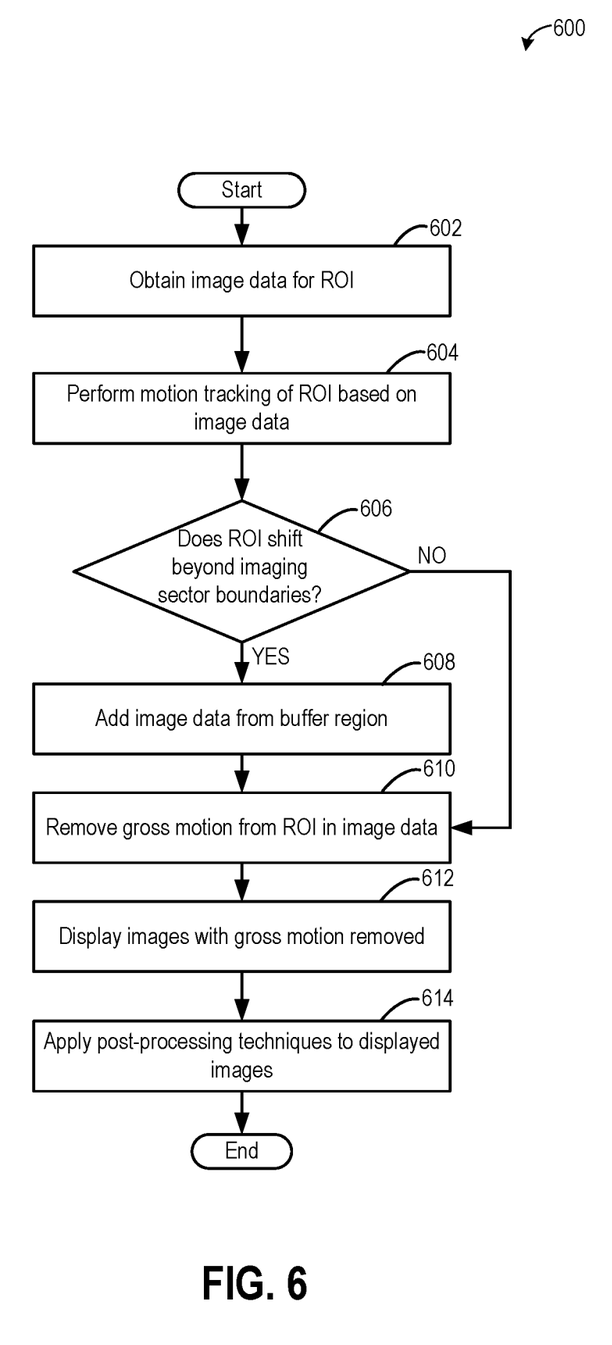
FIG. 6 shows an example of a method for processing and displaying the imaging data collected from the method of FIG. 5.

An example of a method 500 for live imaging data acquisition with tailored motion tracking is shown in FIG. 5 and a method 600 for post-processing and display of the live imaging data is depicted in FIG. 6. Method 500 may be applied to a process for data acquisition, e.g., image capture by a device such as an ultrasound probe, by an imaging system, such as an ultrasound imaging system. Instructions for carrying out methods 500 and 600 may be executed by a system controller, such as the system controller 116 of FIG. 1, based on instructions stored on a memory of the controller and in conjunction with signals received from sensors of the imaging system, such as the motion sensors 107 of FIG. 1.

Turning first to method 500, the method includes identifying a ROI within an imaging sector of the ultrasound probe at 502. The ROI may be identified by, for example, an image recognition module such as the image-recognition module 130 of FIG. 1. The imaging sector may define an image that is displayed to a user, in real-time and post-processing, and may be selected to produce images with a highest level of beam density for a given beam angle, where the beam angle is related to a size of a target region or object to be imaged. In one example, image processing algorithms of the image recognition module may be used in real-time to locate boundaries, borders, contours, or surfaces within an image or a set of images which defines a shape of the ROI. The ROI may thereby be tracked in real-time during live image acquisition.

At 504, the method includes confirming if gross motion is detected. For example, gross motion of the ROI, or of the probe itself, may be detected. In one example, the ROI may move without movement of the probe, e.g., shifting of internal organs. In another example, the probe may be moved, causing the ROI to appear to move within the imaging sector. In other examples, both the ROI and the probe may move. Regardless of the source of movement, the ROI may move within the imaging sector which may be detected by analysis of the image, e.g., by speckle tracking, or by motion sensors of the probe, such as the motion sensors 107 of FIG. 1.

If gross motion is not detected, the method continues to 506 to collect data from within the imaging sector of the probe. Collecting the data may include acquiring images of the ROI according to a selected acquisition mode, frame rate, resolution/beam density, etc. The method proceeds to 514 to store the data, as described further below.

Returning to 504, if gross motion is detected, the method continues to 508 to determine if a magnitude of the gross motion is estimated to be greater than a threshold. The threshold may be an amount of movement at the ROI, e.g., translation of the ROI, which estimated to maintain the ROI within boundaries of the imaging sector. In other words, the threshold may be an estimated margin of allowable movement that the ROI can exhibit without being at least partially displaced outside of the imaging sector. For example, the threshold may be an angular or lateral distance between an outer edge of the ROI and an outer edge of the imaging sector in an initial acquired frame where the ROI is centered in the image.

If the amount of estimated and/or detected gross motion is not greater than the threshold, the method continues to 506 to collect the data from within the imaging sector. If the amount of estimated and/or detected gross motion is greater than the threshold, the method proceeds to 510 to determine a suitable buffer region to apply to the imaging sector. For example, the magnitude of the gross motion may be estimated, based on a signal from the motion sensors and/or based on speckle tracking in real-time, and a target cross sectional-area of the buffer region, extending beyond, e.g., outside of, the boundaries of the initial imaging sector may be selected. The target cross-sectional area may be a balance between providing a sufficiently large area, e.g., beam angle, to maintain the ROI within the buffer region in spite of the gross motion, while minimizing a corresponding decrease in beam density.

In one example a maximum area of the buffer area may be determined based on an effect of an increase in the area on image resolution and/or frame rate. For example, the frame rate may be maintained fixed and a spacing between transmitted beams may be increased by 10%, corresponding to a 10% lower resolution. The maximum area may therefore be an increase of 10%. Alternatively, the beam spacing (and resolution) may be maintained fixed and the frame rate may be decreased by up to 10%. By decreasing the frame rate, more beams may be added to the imaging sector, thereby allowing the imaging sector to be increased up to 10% (by adding the buffer region). Furthermore, a combination of varying the resolution and the frame rate may be used to determine the maximum area of the buffer region.

In one example, the buffer region may be applied to each image frame collected during image acquisition. For example, detection and analysis of the gross motion may be initially conducted to determined settings for subsequent image acquisition, the settings including the beam angle and density employed. The buffer region may be a static parameter, e.g., a suitably wider beam angle may be determined that enlarges an area from which imaging data is collected without localization, as shown in FIG. 3. In other words, data collection may be increased along every dimension equally.

In another example, the buffer region may be instead applied dynamically with a bias to collect additional data from a specific region where gross motion is estimated to occur. For example, the buffer region may be adjusted as shown in FIG. 4, to encompass an area to which the ROI is estimated to shift at least temporarily. The biased buffer region may be applied to each image frame collected during image acquisition. By applying the biased buffer region, a loss of resolution may be decreased relative to use of a buffer region that is applied similarly to each dimension. However, an initial analysis duration may be longer and more complex. In some examples, the application of the biased buffer region may vary, e.g., whether the frame rate or resolution is adjusted or whether the buffer region is fixed or applied dynamically, depending on how the acquired imaging data is to be used and may be selected by the user.

In yet another example, the buffer region may be applied in real-time to image frames where the ROI is detected to move outside of the imaging sector. Real-time deployment of the buffer region may enable a maximum image resolution and frame rate, while reducing an amount of data and a corresponding memory storage space demand. However, the real-time application may cause temporally varying image resolution and/or frame rate.

At 512, the method includes collecting data via the wider beam angle, e.g., from both the imaging sector and the buffer region. Collecting the data may include acquiring images of the ROI according to a selected acquisition mode, frame rate, a resolution/beam density corresponding to the wider beam angle, etc. The data is stored at 514. Storing the data may include, for example, storing the collected data at a memory of the system controller, such as the memory 114 and/or 120 of FIG. 1, in a suitable format with respect to an image-processing module, e.g., the image-processing module 122, of the system controller. The method ends.

Turning now to FIG. 6, method 600 depicts an example of how the imaging data, such as the data collected and stored via method 500 of FIG. 5, may be post-processed. At 602, the method includes obtaining imaging data collected for a ROI, e.g., the ROI of method 500. Obtaining the imaging data may include retrieving the data from a memory of the system controller, e.g., the memory 114 and/or 120 of FIG. 1, and sending the data to a tracking module of the system controller, such as the tracking module 128 of FIG. 1. In one example, the imaging data may be imaging data acquired via method 500 of FIG. 5. The imaging data may include a first set of imaging data obtained from within the imaging sector and a second set of imaging data collected from a buffer region offset from the imaging sector, the second set of data collected in response to detection of motion at the ROI.

At 604, the method include tracking motion at the ROI based on the retrieved first set of imaging data. For example, the ROI may be identified via an analysis module of the system controller, as described above with reference to 502 of method 500. A position of the ROI within an imaging sector of the imaging data may be monitored across a set of images corresponding to the retrieved imaging data.

At 606, the method includes confirming if the ROI shifts beyond, e.g., outside of boundaries of the imaging sector across the set of images. Determination of whether the ROI moves outside of the boundaries of the imaging sector may be provided by an analysis module, such as the image recognition module 130 of FIG. 1. Shifting of the ROI beyond the boundaries may include at least a portion of the ROI moving outside of the imaging sector. If the ROI is determined to not move outside of the imaging sector, the method proceeds to 610 to remove gross motion from the ROI in the imaging data, as described below without adding information from the second set of data to the first second of data.

If the ROI is confirmed to move outside of the imaging sector in any image of the set of images, the method continues to 608 to add information from the second set of imaging data. For example, as described in method 500 of FIG. 5, detection of gross motion during image acquisition may lead to widening of the beam angle to collect additional data outside of the imaging sector during an imaging session. The collected additional data, e.g., as provided by the second set of imaging data, may be used to supplement data corresponding to image frames where the ROI moves outside of the imaging sector. In other words, the additional data may provide data missing from within the imaging sector with respect to obtaining a complete image of the ROI when the ROI is maintained in a fixed position for display.

At 610, the method includes removing the gross motion, if present, from the ROI in the acquired images. Removing the gross motion may include using motion compensation algorithms implemented at a tracking module of the system controller. For example, the first set of imaging data from within the imaging sector supplemented by the additional data from the second set of imaging data may be fed to the motion compensation algorithms. An overall gross motion of the ROI may be determined using a displacement field, which may estimate an amount of deformation of shape change of the ROI. The deformation or shape change may represent the gross motion of the ROI. The gross motion may be compensated for by subtracting the overall motion or deformation from the image data set, thereby removing an average motion from the images of the ROI to be displayed. In some examples, the images of the ROI may be scaled, rotated/and or translated based on the gross motion. In one example, an affine transformation of the images may be performed, which includes a transformation between two vector spaces that includes a linear transformation followed by a translation. However, other methods and techniques for motion compensation may be used without departing from a scope of the present disclosure.

At 612, the method includes displaying the images with the gross motion removed. As an example, the images may be presented as a cine loop and removal of the gross motion allows the ROI to appear stationary, e.g., unmoving and in a fixed position within the imaging sector, as the image frames of the cine loop are displayed and cycled. The buffer region is not shown in the image frames of the cine loop. By selectively incorporating the additional imaging data provided by application of the buffer region, the ROI display is stable through the cine loop, e.g., the ROI image does not skip or momentarily appear to be missing data.

At 614, post-processing of the images may be conducted. For example, speckle tracking, border detection, etc., may be applied to the images with the gross motion removed. Alternatively, in other examples, the post-processing may be performed without the gross motion removed. Instead, the post-processing may be applied directly to the imaging data with data from the buffer region added (e.g., 610 and 612 are omitted). The method ends.

In this way, a complete imaging data set may be obtained, enabling stable live display of the imaging data set to a user. By collecting additional imaging data outside of a visible sector of an imaging device's FOV, gross motion of an imaging ROI may be tracked and the additional imaging data may be used to supplement data corresponding to portions of the ROI that are displaced outside of the visible sector during live image acquisition. Compensation for missing data via modeling is precluded and presentation of the images for efficient analysis and assessment is enabled.

The technical effect of collecting additional data from a buffer region outside of the visible sector of an imaging system is that, responsive to detection of gross motion that leads to the ROI being at least partially displaced outside of the visible sector, an acquisition beam angle of the imaging system is widened, thereby enabling collection of a larger imaging data set while maintaining a consistent display of the ROI in an imaging loop presented to a user.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The disclosure also provides support for a method for motion compensation in live images, comprising: acquiring a first set of imaging data from a visible sector of an imaging system, the visible sector including a region of interest displayed to a user, acquiring a second set of imaging data, at an area offset from the visible sector, during the acquiring of the first set of imaging data, and using the second set of imaging data to compensate for gross motion of the region of interest resulting in displacement of at least a portion of the region of interest outside of the visible sector. In a first example of the method, using the second set of imaging data to compensate for gross motion of the region of interest includes feeding the second set of imaging data to motion compensation algorithms implemented at a system controller of the imaging system. In a second example of the method, optionally including the first example, the method further comprises: estimating the gross motion of the region of interest in the first set of imaging data and wherein estimating the gross motion of the region of interest includes detecting motion at motion sensors of an imaging device of the imaging system. In a third example of the method, optionally including one or both of the first and second examples, the method further comprises: estimating the gross motion of the region of interest in the first set of imaging data based on analysis of the live images and wherein the analysis of the live images is performed using motion compensation algorithms. In a fourth example of the method, optionally including one or more or each of the first through third examples, using the second set of imaging data to compensate for gross motion of the region of interest includes using the second set of imaging data to supplement missing portions of data from the first set of imaging data, the missing portions resulting from the displacement of at least the portion of the region of interest outside of the visible sector. In a fifth example of the method, optionally including one or more or each of the first through fourth examples, acquiring the second set of data at the area offset from the visible sector includes widening a beam angle of an imaging device used to acquire both the first set of data and the second set of data.

The disclosure also provides support for an imaging system, comprising: an imaging device configured to acquire images of a region of interest within a visible sector of the imaging device, and a system controller configured with executable instructions stored on non-transitory memory that, when executed, cause the system controller to: collect a first set of imaging data from a region offset from the visible sector, in response to detection of gross motion at the region of interest, in addition to a second set of imaging data collected from the visible sector, and utilize the first set of imaging data to supplement data missing from the second set of imaging data, to display processed images based on the second set of imaging data. In a first example of the system, the imaging device further includes motion sensors embedded at the imaging device and wherein the motion sensors are configured to detect the gross motion at the region of interest. In a second example of the system, optionally including the first example, the gross motion at the region of interest is detected by motion tracking algorithms implemented at a tracking module of the system controller and wherein the motion tracking algorithms include one or more of speckle tracking, contour tracking, and optical flow. In a third example of the system, optionally including one or both of the first and second examples, the region offset from the visible sector includes an area extending outside of boundaries of the visible sector. In a fourth example of the system, optionally including one or more or each of the first through third examples, the region offset from the visible sector is adjusted to collect the first set of imaging data from an area where movement of the region of interest is estimated to occur and wherein the movement is estimated based on one or more of speckle tracking, border tracking, and a priori knowledge of a shape of the region of interest. In a fifth example of the system, optionally including one or more or each of the first through fourth examples, the processed images displayed based on the second set of imaging data are displayed in a cine loop and wherein the second set of imaging data is processed to present the region of interest in a fixed position in the cine loop. In a sixth example of the system, optionally including one or more or each of the first through fifth examples, the first set of imaging data is used to supplement the data missing from the second set of imaging data during display of the processed images in the cine loop when the region of interest moves outside of the visible sector. In a seventh example of the system, optionally including one or more or each of the first through sixth examples, the first set of data is collected concurrent with the second set of data and wherein only the second set of data showing the region of interest in the visible sector with the gross motion removed is displayed. In a eighth example of the system, optionally including one or more or each of the first through seventh examples, the gross motion is removed using motion compensation algorithms. In a ninth example of the system, optionally including one or more or each of the first through eighth examples, the imaging device is an ultrasound probe and wherein a beam density used to acquire the images of the region of interest and an amount of data provided by the first set of imaging data is adjusted based on a type of the ultrasound probe.

The disclosure also provides support for an ultrasound imaging system, comprising: a first set of imaging data acquired in addition to a second set of imaging data, the first set of imaging data acquired in response to detection of gross motion at a region of interest displayed in the second set of imaging data, and wherein the first set of imaging data is fed to motion compensation algorithms to supplement an omission of data from the second set of imaging data resulting from the gross motion at the region of interest. In a first example of the system, the first set of imaging data is acquired from a buffer region outside of a visible sector from which the second set of imaging data is acquired, and wherein the buffer region is determined based on an estimation of a magnitude of the gross motion and a desired image resolution. In a second example of the system, optionally including the first example, the second set of imaging data is displayed as processed images of the region of interest within the visible sector to a user and the buffer region is not displayed. In a third example of the system, optionally including one or both of the first and second examples, the second set of imaging data is displayed as the processed images of the region of interest as a cine loop and wherein the cine loop is displayed without skipping and the region of interest is shown in each image frame of the cine loop with a size similar to an area of the visible sector.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for motion compensation in live images, comprising:
    acquiring a first set of imaging data from a visible sector of an imaging system, the visible sector including a region of interest displayed to a user;
    acquiring a second set of imaging data, at an area offset from the visible sector, during the acquiring of the first set of imaging data; and
    using the second set of imaging data to compensate for gross motion of the region of interest resulting in displacement of at least a portion of the region of interest outside of the visible sector, wherein using the second set of imaging data to compensate for gross motion of the region of interest includes using the second set of imaging data to supplement missing portions of data from the first set of imaging data, the missing portions resulting from the displacement of at least the portion of the region of interest outside of the visible sector.

2. The method of claim 1, wherein using the second set of imaging data to compensate for gross motion of the region of interest includes feeding the second set of imaging data to motion compensation algorithms implemented at a system controller of the imaging system.

3. The method of claim 1, further comprising estimating the gross motion of the region of interest in the first set of imaging data and wherein estimating the gross motion of the region of interest includes detecting motion at motion sensors of an imaging device of the imaging system.

4. The method of claim 1, further comprising estimating the gross motion of the region of interest in the first set of imaging data based on analysis of the live images and wherein the analysis of the live images is performed using motion compensation algorithms.

5. The method of claim 1, wherein acquiring the second set of data at the area offset from the visible sector includes widening a beam angle of an imaging device used to acquire both the first set of data and the second set of data.

6. An imaging system, comprising:
    an imaging device configured to acquire images of a region of interest within a visible sector of the imaging device; and
    a system controller configured with executable instructions stored on non-transitory memory that, when executed, cause the system controller to:
        collect a first set of imaging data from a region offset from the visible sector, in response to detection of gross motion at the region of interest, in addition to a second set of imaging data collected from the visible sector; and
        utilize the first set of imaging data to supplement data missing from the second set of imaging data, to display processed images based on the second set of imaging data.

7. The imaging system of claim 6, wherein the imaging device further includes motion sensors embedded at the imaging device and wherein the motion sensors are configured to detect the gross motion at the region of interest.

8. The imaging system of claim 6, wherein the gross motion at the region of interest is detected by motion tracking algorithms implemented at a tracking module of the system controller and wherein the motion tracking algorithms include one or more of speckle tracking, contour tracking, and optical flow.

9. The imaging system of claim 6, wherein the region offset from the visible sector includes an area extending outside of boundaries of the visible sector.

10. The imaging system of claim 6, wherein the region offset from the visible sector is adjusted to collect the first set of imaging data from an area where movement of the region of interest is estimated to occur and wherein the movement is estimated based on one or more of speckle tracking, border tracking, and a priori knowledge of a shape of the region of interest.

11. The imaging system of claim 6, wherein the processed images displayed based on the second set of imaging data are displayed in a cine loop and wherein the second set of imaging data is processed to present the region of interest in a fixed position in the cine loop.

12. The imaging system of claim 11, wherein the first set of imaging data is used to supplement the data missing from the second set of imaging data during display of the processed images in the cine loop when the region of interest moves outside of the visible sector.

13. The imaging system of claim 6, wherein the first set of data is collected concurrent with the second set of data and wherein only the second set of data showing the region of interest in the visible sector with the gross motion removed is displayed.

14. The imaging system of claim 13, wherein the gross motion is removed using motion compensation algorithms.

15. The imaging system of claim 6, wherein the imaging device is an ultrasound probe and wherein a beam density used to acquire the images of the region of interest and an amount of data provided by the first set of imaging data is adjusted based on a type of the ultrasound probe.

16. An ultrasound imaging system, comprising:
    a first set of imaging data acquired in addition to a second set of imaging data, the first set of imaging data acquired in response to detection of gross motion at a region of interest displayed in the second set of imaging data, and wherein the first set of imaging data is fed to motion compensation algorithms to supplement an omission of data from the second set of imaging data resulting from the gross motion at the region of interest.

17. The ultrasound imaging system of claim 16, wherein the first set of imaging data is acquired from a buffer region outside of a visible sector from which the second set of imaging data is acquired, and wherein the buffer region is determined based on an estimation of a magnitude of the gross motion and a desired image resolution.

18. The ultrasound imaging system of claim 17, wherein the second set of imaging data is displayed as processed images of the region of interest within the visible sector to a user and the buffer region is not displayed.

19. The ultrasound imaging system of claim 18, wherein the second set of imaging data is displayed as the processed images of the region of interest as a cine loop and wherein the cine loop is displayed without skipping and the region of interest is shown in each image frame of the cine loop with a size similar to an area of the visible sector.

* * * * *